US010035990B2

(12) United States Patent
Paramelle et al.

(10) Patent No.: US 10,035,990 B2
(45) Date of Patent: Jul. 31, 2018

(54) SPECIFIC INTERNALIZATION OF NANOPARTICLES INTO PROTEIN CAGES

(71) Applicants: Agency for Science, Technology and Research, Singapore (SG); Nanyang Technological University, Singapore (SG)

(72) Inventors: David Paramelle, Singapore (SG); Nikodem Tomczak, Singapore (SG); Paul Free, Singapore (SG); Sierin Lim, Singapore (SG); Tao Peng, Singapore (SG)

(73) Assignees: Agency for Science, Technology, and Research, Singapore (SG); Nanyang Technological University, Singapore (SG)

( * ) Notice: Subject to any disclaimer, the term of this patent is extended or adjusted under 35 U.S.C. 154(b) by 138 days.

(21) Appl. No.: 14/651,626

(22) PCT Filed: Dec. 10, 2013

(86) PCT No.: PCT/SG2013/000521
§ 371 (c)(1),
(2) Date: Jun. 11, 2015

(87) PCT Pub. No.: WO2014/092646
PCT Pub. Date: Jun. 19, 2014

(65) Prior Publication Data
US 2015/0329836 A1 Nov. 19, 2015

(30) Foreign Application Priority Data
Dec. 12, 2012 (SG) .................................. 201209135

(51) Int. Cl.
*C12N 9/10* (2006.01)
*C12Q 1/48* (2006.01)
*C12N 9/96* (2006.01)
*B82Y 40/00* (2011.01)
*B82Y 5/00* (2011.01)

(52) U.S. Cl.
CPC ............ *C12N 9/1029* (2013.01); *B82Y 40/00* (2013.01); *C12N 9/96* (2013.01); *C12Q 1/48* (2013.01); *C12Y 203/01012* (2013.01); *B82Y 5/00* (2013.01); *G01N 2333/91057* (2013.01); *Y10T 428/2991* (2015.01); *Y10T 428/2998* (2015.01)

(58) Field of Classification Search
CPC ........ B82Y 40/00; B82Y 5/00; C12N 9/1029; C12N 9/96; C12Q 1/48; C12Y 203/01012; G01N 2333/91057; Y10T 428/2991; Y10T 428/2998
USPC ................ 428/407; 435/15, 188, 193; 506/7
See application file for complete search history.

(56) References Cited

U.S. PATENT DOCUMENTS

| 8,343,497 B2 * | 1/2013 | Shi .......................... A61K 39/00 424/184.1 |
| 2004/0028694 A1 * | 2/2004 | Young .................. A61K 9/5169 424/190.1 |

FOREIGN PATENT DOCUMENTS

WO 2008/124165 A2 10/2008

OTHER PUBLICATIONS

Jutz et al., "Bionanoparticles as functional macromolecular building blocks—A new class of nanomaterials," *Polymer* 52:211-232, 2011.
Lim et al., "Protein Cages as Theranostic Agent Carriers," World Congress on Medical Physics and Biomedical Engineering, May 26-31, 2012, Beijing, China, pp. 321-324.
Saini et al., "An Adenoviral Platform for Selective Self-Assembly and Targeted Delivery of Nanoparticles," *Small* 4(2):262-269, 2008.
Dalmau et al., "pH-Triggered Disassembly in a Caged Protein Complex," *Biomacromolecules* 10:3199-3206, 2009.

* cited by examiner

*Primary Examiner* — Janet L Epps-Smith
(74) *Attorney, Agent, or Firm* — Seed IP Law Group LLP

(57) ABSTRACT

The invention relates to a method to encapsulate nanoparticles into a protein cage by inserting the nanoparticles into the core through holes. Currently commercially available nanoparticles can be functionalized using the inventive method. The inventive hybrids have applications in biosensing and bioimaging. The use of an affinity between polyhistidine chains and nitrilotriacetic acid as chelating reagent to obtain the inventive cages and hybrid assemblies by the method according to the invention is shown in FIG. 1.

8 Claims, 4 Drawing Sheets

SPECIFIC INTERNALIZATION OF NANOPARTICLES INTO PROTEIN CAGES

TECHNICAL FIELD

The present invention generally relates to methods for making hybrid assemblies of nanoparticles into protein cages by encapsulation. Such bioinorganic hybrids are useful in many technical fields such as for instance bioimaging and biosensing.

BACKGROUND

There are currently two major routes available for the preparation of encapsulated nanoparticles inside protein cages:

There are the self-assembly of the cages in presence of synthesized and appropriately functionalized nanoparticles and the in-situ synthesis of nanoparticles inside protein cages (Aniagyei S. E. et al., J. Mater. Chem., 2008, 18, 3763-3774).

The self-assembly route inherently requires the protein cage to be able to undergo reversible disassembly and reformation in presence of the nanoparticles, i.e., once the protein cage is broken up it should be possible to reconstitute it back. The method is clearly not applicable to protein cages that disassemble irreversibly.

The in-situ growth of nanoparticles inside protein cages, although by far the most popular method, has limits related to the growth of nanoparticles in confinement. In most cases accurate control over the morphology of the nanoparticles is impaired. Surface effects become dominant and the bulk properties of the assemblies display broader distributions. For example, growth induced from multiple nucleation sites results in polycrystalline nanoparticles, which in case of semiconductor nanocrystals results in inferior optical properties compared to presynthesized quantum dots (QDs). Growing passivating inorganic shells like in CdSe/ZnS is virtually impossible due to the restricted access to the surface of the nanoparticles after the synthesis. One would also desire a material where the stoichiometric ratio between the nanoparticle and the protein cage is equal to 1. This is in particular important in particle tracking, bioimaging and biosensing, where the knowledge of stoichiometry would allow one to perform quantitative analysis.

There is a need to provide new methods for encapsulating the nanoparticles in protein cages to overcome the above mentioned limitations.

SUMMARY

According to a first aspect, there is a method for internalization of nanoparticles into protein cages comprising the following steps
 (i) modifying a protein cage at predefined locations,
 (ii) functionalizing nanoparticles to be able to bind at specific predefined locations of the protein cage, and
 (iii) introducing the nanoparticles through holes in the protein cage.

Advantageously, this method can be utilized for encapsulation of the nanoparticles without disassembly of the cages and without any need for in-situ synthesis of the nanoparticles.

Further advantageously, the nanoparticle is able to diffuse into the protein cage and bind to modified parts of the protein cage without disturbing the protein structure.

According to a second aspect, a method has been found wherein the protein cage is genetically modified at predefined locations with one or more sequences of aminoacids, e.g., histidines.

Advantageously, sequences of histidines allow for the insertion of nanoparticles, e.g., gold nanoparticles, functionalized by nitrilotriacetic acid (NTA) or tris-NTA (TNTA).

According to the third aspect, a protein cage genetically modified at predefined locations with one or more sequences of histidines has been provided.

Advantageously, such protein cages can be used to insert nanoparticles into them which are functionalized by one or more ligands selected from nitrilotriacetic acid, a multiple nitrilotriacetic acid and their derivatives.

According to the fourth aspect, a nanoparticle coated with ligands which are able to bind to histidines of the genetically modified protein cages has been obtained according to the invention.

Advantageously, these presynthesized nanoparticles are able to be inserted into the protein cage according to the invention via holes without any need of protein cage disassembly.

According to the fifth and sixth aspect, a hybrid assembly obtained by inserting a nanoparticle according to the invention into a protein cage according to the invention or a hybrid assembly made according to a method according to the invention has been provided together with its use.

Advantageously, such hybrids can be obtained even for nanoparticles which would otherwise not be able to be inserted into the protein cages and their uses have been made possible.

Definitions

The following words and terms used herein shall have the meaning indicated:

The word "substantially" does not exclude "completely", e.g., a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of the invention will now be disclosed.

According to a first aspect, there is a method for internalization of nanoparticles into protein cages comprising the following steps (i) modifying a protein cage at predefined locations, (ii) functionalizing nanoparticles to be able to bind at specific predefined locations of the protein cage, and (iii) introducing the nanoparticles through holes in the protein cage.

According to this method the modification of the protein is preferably done by genetically engineering. Such methods are widely known (Dalmau, M. et al., *Biotechnol. Bioeng.* 2008, 101, 654-64; Ren, D. et al., *Adv. Funct. Mater.* 2012, 22, 3170-3180).

Functionalization of the nanoparticle can be done by suitable presynthesis (e.g. coating with suitable ligands) that enable the binding of the nanoparticle to the specific predefined locations of the protein cage.

According to a second aspect, the protein cage is genetically modified at predefined locations with one or more sequences of histidines. Preferably the sequence of histidine is a polyhistidine chain of two or more histidines. The affinity between histidine moieties and certain ligands can be used according to the invention to achieve the binding in the protein cage.

According to another aspect of the invention a method wherein the nanoparticles are coated with ligands, preferably surface mono-, bi- and multivalent metal chelators, for example bivalent nickel or cobalt chelating ligands such as iminodiacetic acid and nitrilotriacetic acid, which are able to bind to the histidines can then be combined with such genetically modified protein cage. According to another aspect of the invention a surface ligand is selected from nitrilotriacetic acid, a multiple nitrilotriacetic acid and their derivatives. Nitrilotriacetic (NTA) and tris-NTA (TNTA) are particularly preferred.

NTA, TNTA and their derivatives and their ligand functions and poly-histidine sequences affinity are known (E. Hochuli et al. Nature Biotechnology 1988, 6, 1321-1325; Huang, Z. et al., Bioconjug. Chem. 2009, 20, 1667-72).

According to the instant invention a new route for specific internalization of NTA-functionalized coated nanoparticles into protein cages mutated with various poly-histidine sequences at the inner part of their structure has been found.

According to the invention all kinds of nanoparticles can be used, including for instance also quantum dots (QD) and superparamagnetic iron oxide nanoparticles (SPIONs). Preferably the nanoparticle is a metal, a metal oxide, an elemental or compound semiconductor, a polymer, an elemental cluster or a nanodiamond. A compound semiconductor is a semiconductor compound composed of elements from two or more different groups of the periodic table. A nanodiamond is a nanocrystalline form of diamond.

Most preferably the nanoparticle is a gold or silver nanoparticle.

According to another aspect of the instant invention, the protein cage is made from the protein dihydrolipoyl acetyltransferase, but is not limited to such protein cage. The dihydrolipoyl acetyltransferase (E2) is an enzyme of the pyruvate dehydrogenase multi-enzyme complex from *Geobacillus stearothermophilus*.

According to the third aspect, a protein cage genetically modified at predefined locations with one or more sequences of histidines has been provided.

Such protein cage can be used in the methods according to the invention.

A protein cage according to the invention which after assembly displays accessible histidine residues in the interior surface of the cage is preferred. The display of accessible histidine means that a binding with corresponding ligands (e.g. NTA or TNTA) in the inside of the cage is especially strong.

A preferred protein is a dihydrolipoyl acetyltransferase (E2) mentioned in relation to the inventive methods.

According to the fourth aspect of the invention a nanoparticle coated with ligands which are able to bind to poly-histidine sequences has been prepared and is claimed herewith. Typical nanoparticles can comprise a metal, a metal oxide, an elemental or compound semiconductor, a polymer, an elemental cluster or a nanodiamond, but there is no limitation to such nanoparticles. In general all nanoparticles of suitable size can be used according to the invention.

The nanoparticles have a preferred size of 1 to 50 nm. Most preferably they have a size of about 1-25 nm. The nanoparticles have a size and shape allowing direct internalization inside the protein cage via holes.

In a fifth aspect according to the invention, a hybrid assembly obtained by inserting a nanoparticle according to the invention into a protein cage according to the invention or a hybrid assembly made according to a method according to the invention has been prepared. The hybrid assembly consists of a nanoparticle encapsulated in a protein cage.

According to a sixth aspect of the invention, the hybrid assemblies have a use in bioimaging, biosensing and signal multiplexing. The protein/nanoparticles assemblies can be directly applied in bioimaging and biosensing where the protein shell provides biocompatibility and colloidal stability, and the encapsulated nanoparticle is a signal generator (light generation), transducer (optical modulation), or act as intermediate (via e.g. electron transfer processes (Soto C. M., Ratna B. R., Curr. Op. Biotechnol., 2010, 21, 426-438). The use of monodisperse nanoparticles allows for efficient signal multiplexing. When the encapsulated nanoparticles are made of catalytically active compounds the described materials can be employed in catalysis in aqueous dispersions (Mori K., Yamashita H., PhysChemChemPhys, 2010, 12, 14420-14432)

The materials described herein may find also application in nanoelectronics as elements of nanoscale memory devices, e.g. floating nanodot gate memory (Yamashita I., J. Mater. Chem., 2008, 18, 3813-3820).

Some other aspects of the invention are further mentioned:

A protein cage genetically modified at predefined locations with sequence of histidines in number of 1 and higher.

A protein cage, which is able to correctly assemble after the genetic modification.

A protein cage as described above, which displays accessible histidine residues in the interior surface of the cage.

A presynthesized nanoparticle coated with surface ligands, which are providing colloidal stability and are able to bind to the histidine sequences in the protein cage. The nanoparticles may include Au, Ag and other metals, metal oxides, elemental and compound semiconductors, polymers, elemental clusters, nanodiamonds etc.

A nanoparticle as described above has a size and shape allowing direct internalization inside the protein cage via its holes.

A hybrid assembly made of the nanoparticle described above, and a protein cage described above.

Such hybrid assembly is obtained without the disassembly of the protein cages and without any in-situ chemical reaction during the assembly except supramolecular binding of the nanoparticle surface ligands to the genetically modified protein sequences inside the protein cages.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

EXAMPLES

Non-limiting examples of the invention and a comparative example will be further described in greater detail by reference to specific Examples, which should not be construed as in any way limiting the scope of the invention.

EXAMPLES

Mutation of the Protein Cage Model E2

See the following literature:
M. Dalmau, S. Lim, H. C. Chen, C. Ruiz, S. W. Wang, Biotechnology and Bioengineering 2008, 101, 654-664, M. Dalmau, S. R. Lim, S. W. Wang, Nano Letters 2009, 9, 160-166)

The protein is the enzyme dihydrolipoyl acetyltransferase (E2) of the pyruvate dehydrogenasemulti-enzyme complex from *Geobacillus stearothermophilus*. The E2 protein subunits self-associate into a dodecahedron cage forming a hollow core that consists of 60 identical units. The hollow core can potentially be utilized for molecular encapsulation. Its three-dimensional structure shows this assembly is approximately 24 nm in diameter with 12 openings of about 5 nm each. These openings were used for internalization of well-designed and functionalized nanoparticles.

Figure 1:
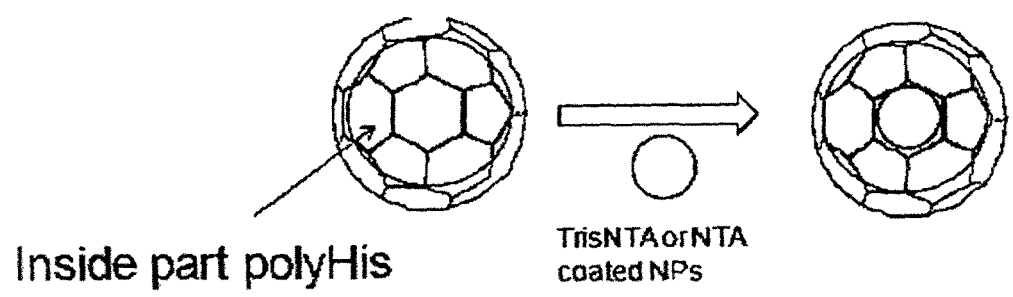
FIG. 1. Internalization of NTA functionalized coated nanoparticles into poly-histidine mutated protein cages FIG. 2. (A) Single E2 subunit with RDGE loop highlighted by different shade. (B) Highlighted RDGE loop on the inner surface of the half E2 protein cage (30 subunits).
Figure 2:
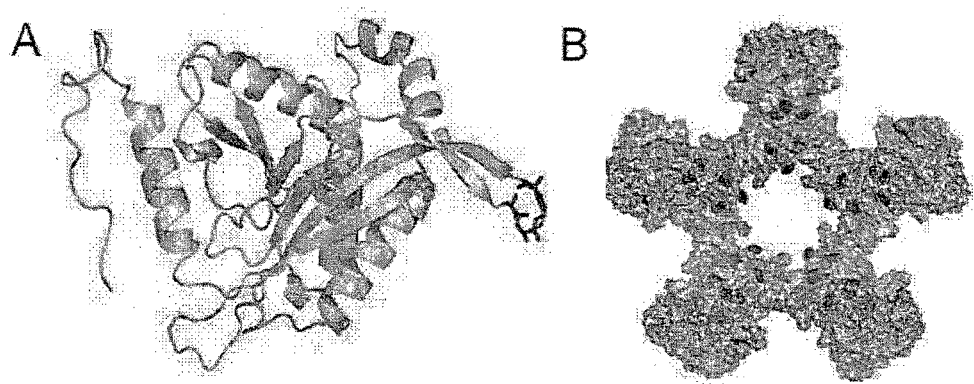

To guide the nanoparticles specifically inside the protein cages, according to the invention different mutants of the wild-type E2 protein (E2-WT) were designed. A loop structure located inside the cage was identified as a potential mutation sites (FIG. 2). The residues at this loop structure were replaced with several combinations of histidine residues (LoopHistidine-LH-mutants, LH4, LH 6, and H3LH3).

| E2-WT loop sequence: | WT: . . . $P^{377}$IVRDGEIVA$^{386}$ . . . |
| Mutations with polyHis sequences: | LH5: . . . $P^{377}$IVHHHHHIVA$^{386}$ . . . |
| | LH6: . . . $P^{377}$IVHHHHHHIVA$^{388}$ . . . |

Figure 3:
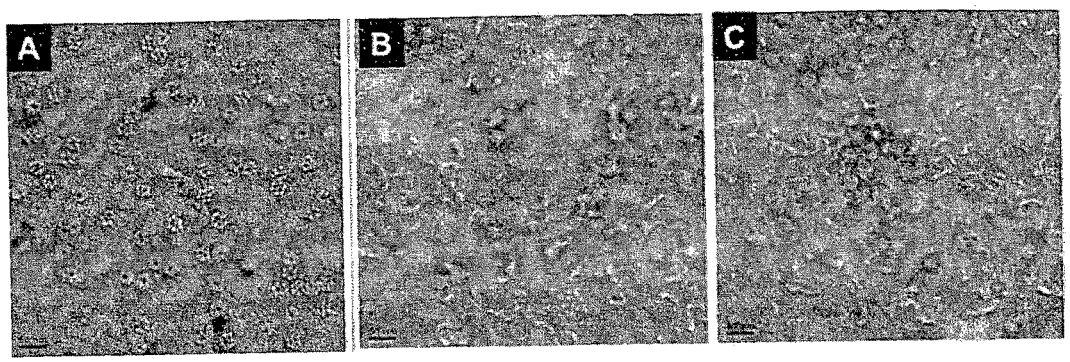
FIG. 3. Electron micrographs of (A) E2-WT at pH 7.4 (stained with 1.5% uranyl acetate) and loop mutants (B) E2-LH5, (C) E2-LH6 (stained with 1% phosphotungstic acid).

DLS (Table 1) and TEM (FIG. 3) results confirmed the correctly assembled spherical structure of E2-LH5 and E2-LH6.

TABLE 1

DLS results of all loop mutants (nm). Results are obtained using size distribution by volume.

| Size distribution by Volume (nm) | Peak 1 | Percentage | Peak 2 | Percentage |
|---|---|---|---|---|
| E2-LH5 | 28.87 | 93.5% | 98.98 | 6.5% |
| E2-LH6 | 31.35 | 98% | 105.6 | 2% |

The slightly larger peak values of E2-LH6 compared to the E2-LH5 are potentially because of variation in the purities of the samples rather than size differences.

According to the invention the functional peptide was inserted to the interior surface of E2 protein cage to replace the original RDGE peptide loop. For all the mutant proteins constructed the incorporation of non-native peptide did not influence the self-assembly of the protein cage structure.

Preparation of NTA Functionalized Coated Nanoparticles

A. Preparation of H-CV$_3$T-ol:HS-C$_{11}$-EG$_4$:HS-C$_{11}$-EG$_3$-NTA 60:30:10 (Mole/Mole/Mole) Coated Gold Nanoparticles (5 nm):

600 µL of 2 mM H-CV$_3$T-ol in water mQ, 300 µL of 2 mM HS-C11-EG4 in water mQ and 100 µL of 2 mM HS-C$_{11}$-EG$_3$-NTA are mixed in a 25 mL glass vial. 50 µL of a 1% Tween 20 in water mQ are added along with 9 mL of citrate colloidal gold (5 nm) and the solution mixed for 10 minutes. 1 mL of PBS buffer 10× (pH 7.4) is added and the solution is mixed overnight at room temperature.

After centrifugation of the nanoparticles (16 Krcm, 1 hour), removal of the solvent and dispersion of the nanoparticles in 500 µL of PBS (pH 7.4), the sample is purified by size exclusion chromatography G25 in 200 mM NaCl aqueous solvent. The nanoparticles collected are concentrated by centrifugation (16 Krcm, 1 hour) and the solvent exchange with PBS (pH 7.4).

The NTA functions of the purified nanoparticles are activated with addition of a 2.8 M Ni(NO$_3$)$_2$ aqueous solution (Ni(II) final concentration of 250 mM) and the sample mixed for 2 hours. The nanoparticles are then purified by size exclusion chromatography G25 in 200 mM NaCl aqueous solvent. The nanoparticles collected are concentrated by centrifugation (16 Krcm, 1 hour) and the solvent exchange with phosphate buffer pH 8 (50 mM NaH$_2$PO$_4$, 0.5 M NaCl). Final concentration of nanoparticles is estimated at 0.4 µM by UV-visible spectrophotometry.

* Preparation of H-CV$_3$T-ol:HS-C$_{11}$-EG$_4$ 70:30 (mole/mole) coated gold nanoparticles stoichiometrically functionalized with HS-C$_{16}$-EG$_3$-TrisNTA (5 nm) can be done analogously.

Internalization of NTA Functionalized and Coated Nanoparticles Inside E2 Protein Cages:

All protein cages are washed twice in water mQ with Nanosep 10K filters and dissolved in a phosphate buffer pH 8 (50 mM NaH$_2$PO$_4$, 0.5 M NaCl). Final concentrations of the protein cages are about 1 µM.

In a 500 µL centrifugation tube, 50 µL of H-CV$_3$T-ol:HS-C$_{11}$-EG$_4$:HS-C$_{11}$-EG$_3$-NTA 60:30:10 (mole/mole/mole) coated gold nanoparticles (5 nm) (at 0.4 µM) are mixed with 50 µL of E2 protein cages (at 1 µM) overnight at room temperature. Samples are then stored in fridge for few days and analyzed by TEM.

Figure 4:
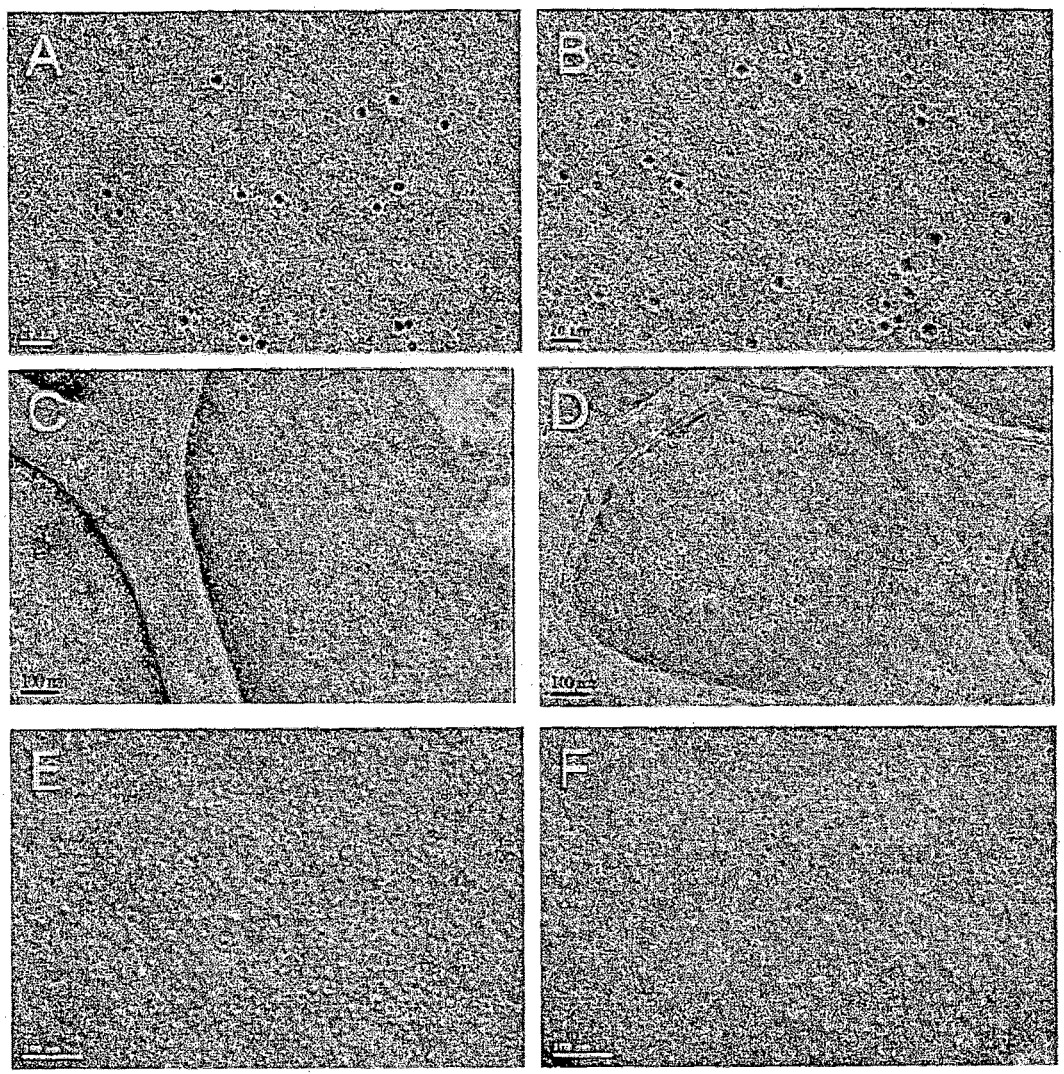
FIG. 4. TEM imaging of internalized NTA functionalized gold nanoparticles 5 nm. A/B) Internalized nanoparticles in LH5 E2 mutants; C/D) Internalized nanoparticles in LH6 E2 mutants; E/F) No internalization of NTA functionalized nanoparticles in wild type E2 protein cages.

UV-Vis, TEM Analysis of Internalization of NTA Functionalized and Coated Nanoparticles Inside E2 Protein Cages:

The images obtained by TEM show evidence of internalization of the nanoparticles inside mutated poly-histidine protein cages (FIG. 4—A, B, C, D).

Purification of Protein Cages Containing Nanoparticles:

Current methods to purify nanoparticles include the use of ultracentrifugation, centrifugal filtration devices, and size-exclusion chromatography. These techniques have been used to purify salts or molecules from the comparatively large nanoparticles. A purification strategy to purify protein cages containing nanoparticles is required. The high density of metal nanoparticles compared to the protein cage may allow centrifugal methods to separate protein from nanoparticles (alone or inside a protein cage). Size-exclusion chromatography may allow further separation of the protein cages containing nanoparticles. Size-exclusion chromatography beads are commercially available to purify globular proteins in the KDa to MDa size range. The synthesis of metal nanoparticles may fit the range of 1-15 nm, with the E2 protein cage approximately 25 nm in size. Using GE Healthcare Sepharose, Sephacryl, or Superdex size-exclusion chromatography media the separation of different sized nanomaterials may be possible. Initial tests with Superdex 200 HR have allowed separating 5 nm from 10 nm nanoparticles, and 10 nm from ~15 nm nanoparticles. Agarose gel electrophoresis has also been used to separate the nanoparticle cages from protein fragments, and is a useful purification or analysis tool.

APPLICATIONS

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method for internalization of nanoparticles into protein cages comprising the following steps:
   (i) modifying a protein cage at predefined locations with one or more residues of histidines to provide accessible histidine residues displayed on an interior surface of the protein cage;
   (ii) functionalizing nanoparticles to be able to bind the one or more residues of histidines; and
   (iii) introducing the nanoparticles through holes in the protein cage; wherein the protein cage is made from dihydrolipoyl acetyltransferase.

2. A method according to claim 1 wherein functionalizing nanoparticles comprises coating the nanoparticles with ligands capable of binding to the one or more residues of histidine.

3. A method according to claim 2 wherein the surface ligand is selected from nitrilotriacetic acid, a multiple nitrilotriacetic acid and their derivatives.

4. A method according to claim 1 wherein the nanoparticle is a metal, a metal oxide, an elemental or compound semiconductor, a polymer, an elemental cluster or a nanodiamond.

5. A method according to claim 4 wherein the nanoparticle is a gold or silver nanoparticle.

6. A dihydrolipoyl acetyltransferase protein cage genetically modified at predefined locations with one or more residues of histidine.

7. A protein cage according to claim 6 which after assembly displays accessible histidine residues in the interior surface of the protein cage.

8. A hybrid assembly obtained by inserting a nanoparticle coated with one or more ligands capable of binding to one or more residues of histidine into a dihydrolipoyl acetyltransferase protein cage modified at predefined locations with one or more residues of histidine, wherein the one or more ligands bind to the one or more residues of histidine.

* * * * *